Jan. 30, 1962 E. S. BOERNER Plant Pat. 2,125
CHRYSANTHEMUM PLANT
Filed March 17, 1961
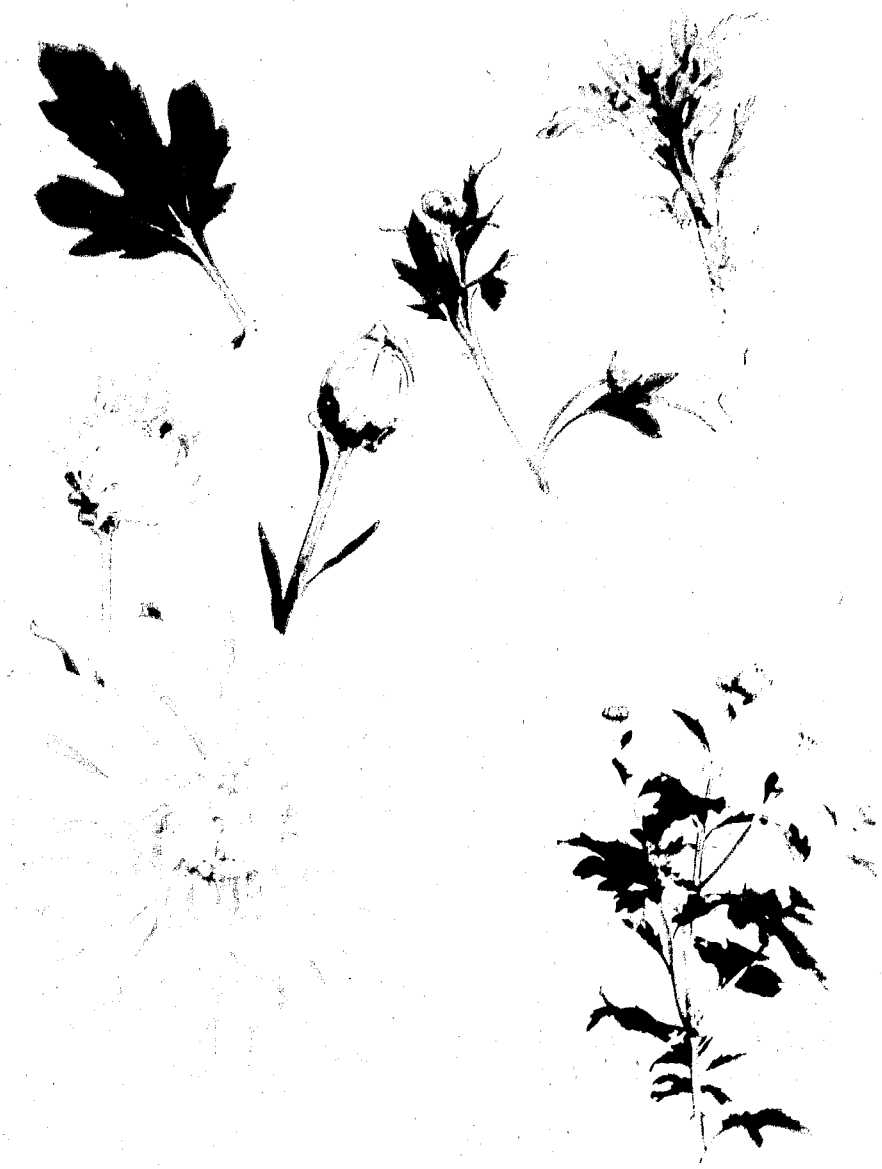
Inventor
E. S. Boerner
By: Robb & Robb
Attorneys United States Patent Office Plant Pat. 2,125
Patented Jan. 30, 1962

2,125
CHRYSANTHEMUM PLANT

Eugene S. Boerner, Newark, N.Y., assignor to Jackson & Perkins Company, Newark, N.Y., a corporation of New York Filed Mar. 17, 1961, Ser. No. 96,627
1 Claim. (Cl. 47—60)

The present invention relates to a new and distinct variety of chrysanthemum plant of the decorative class, which was originated by me by crossing an unnamed and unpatented seedling derived from a cross of "Meadowlark" (Plant Patent No. 1,305) × "Thrush" (Plant Patent No. 1,168) with the variety known as "Martin" (Plant Patent No. 1,466).

The primary objective of this breeding was to produce a new chrsyanthemum variety which combines the earliness and floriferousness of the parent variety "Martin" with the distinctive plant type and size of the unnamed seedling parent. This objective was fully achieved, as evidenced by the following characteristics which are outstanding in the new variety and which distinguish it from its parents, as well as from all other varieties of which I am aware:

(1) An early blooming habit;

(2) A floriferous habit;

(3) A distinctive blooming habit in which successive new blooms are produced above older flowers from late August to frost;

(4) A large flower size; and (5) A distinctive and attractive general color tonality of the flowers corresponding to Light Salmon Orange, lightly overcast with Salmon Orange, which is unusual in a low and compact type of plant.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.

*Seed parent.*—An unnamed seedling of "Meadowlark" × "Thrush."

*Pollen parent.*—"Martin."

Classification: Decorative.

Growth: Low, full.

Cold resistance: Winter hardy in northern New York State.

Blooming period: From late August to frost, with each successive new bloom blooming above the older flowers.

*Flower*

Bud:

*Color.*—When sepals first divide—Zinc Orange, Plate 15. When petals begin to unfurl—Flame Scarlet, Plate 2, with lower half of petals overcast with Orange Buff, Plate 3. When half-blown: inside of petals—Bittersweet Orange, Plate 2, with center of petals lightly overcast with Bittersweet Pink, Plate 2; outside of petals—Salmon Orange, Plate 2.

*Peduncle.* — Color — Biscay Green, Plate 17. Strength—medium.

Bloom:

*Size.*—6½ inches.

*Stem.*—Strong.

*Form.*—Decorative.

*Petalage.*—Double.

*Color.*—Center of flower—Flame Scarlet, Plate 2. Outer petals—Pale Yellow-Orange, Plate 2, lightly overcast with Capucine Orange, Plate 3. Base of petals—Pale Greenish Yellow, Plate 5. Inside of petals—Light Salmon Orange, Plate 2, lightly overcast with Salmon Orange, Plate 2. Reverse of petals—Orient Pink, Plate 2, lightly overcast with Capucine Buff, Plate 3.

*Petals.*—Texture—stiff. Form—petals curl quill-fashion at the finish.

*Fragrance.*—Characteristic chrysanthemum.

*Plant*

Form: Low; compact.

Growth: Full.

Foliage:

*Size.*—Medium.

*Quantity.*—Medium.

*Color.*—Upper side—Varley's Green, Plate 18. Reverse side—Bice Green, Plate 17.

*Eexture.*—Leathery.

I claim:

A new and distinct variety of chrysanthemum plant of the decorative class, substantially as herein shown and described, characterized particularly as to novelty by the unique combination of an early blooming habit, a floriferous habit, a distinctive blooming habit in which successive new blooms are produced above the older flowers from late August to frost, a large flower size, and a distinctive and attractive general color tonality of the flowers corresponding to Light Salmon Orange, lightly overcast with Salmon Orange, and which is unusual in combination with a low and compact plant form.

No references cited.